United States Patent [19]

Hlady et al.

[11] Patent Number: 5,700,953
[45] Date of Patent: Dec. 23, 1997

[54] METHOD FOR MAPPING MECHANICAL PROPERTY OF A MATERIAL USING A SCANNING FORCE MICROSCOPE

[75] Inventors: Vladimir Hlady; Andras Pungor; Eric W. Stroup, all of Salt Lake City, Utah

[73] Assignee: University of Utah Research Foundation, Salt Lake City, Utah

[21] Appl. No.: 627,948

[22] Filed: Apr. 3, 1996

[51] Int. Cl.⁶ .................................................. G01B 5/28
[52] U.S. Cl. ............................................ 73/105; 250/307
[58] Field of Search ........................... 73/105; 250/306, 250/307

[56] References Cited

U.S. PATENT DOCUMENTS

| | | | |
|---|---|---|---|
| 5,168,159 | 12/1992 | Yagi | 250/306 |
| 5,321,977 | 6/1994 | Clabes et al. | 73/105 |
| 5,394,741 | 3/1995 | Kajimura et al. | 250/306 X |
| 5,440,121 | 8/1995 | Yasutake et al. | 250/306 |
| 5,519,212 | 5/1996 | Elings et al. | 73/105 X |

OTHER PUBLICATIONS

Hansma et al., "Tapping Mode Atomic Force Microscopy in Liquids", Appl. Phys. Lett., vol. 64, No. 13, 28 Mar. 1994, pp. 1738–1740.

Hobbs et al., "Atomic Force Microscope: Implementations", SPIE vol. 897 Scanning Microscopy Technologies and Applications, 1988, pp. 26–30.

Martin et al., "Atomic Force Microscope–Force Mapping and Profiling on a Sub 100–Å Scale", J. Appl. Phys., vol. 61, No. 10, 15 May 1987, pp. 4723–4729.

Radmacher et al., "From Molecules to Cells: Imaging Soft Samples with the Atomic Force Microscope", Science, vol. 247, 25 Sep. 1992, pp. 1900–1905.

*Primary Examiner*—Hezron E. Williams
*Assistant Examiner*—Daniel S. Larkin
*Attorney, Agent, or Firm*—Terry M. Crellin

[57] ABSTRACT

The method for mapping a mechanical property of a surface of a sample with a scanning force microscope comprises the steps of (a) scanning a fine tip in contact with the surface of the sample within a predetermined scan area, the fine tip being supported on an end of a cantilever beam, (b) applying a loading force on the surface of the sample by the fine tip, (c) using a constant frequency sine wave to oscillate the cantilever beam relative to the surface of the sample, (d) measuring a detector response of the fine tip at the end of the cantilever beam, (e) determining an amplitude of the detector response and a change in phase angle of the detector response relative to the sine wave used to oscillate the cantilever beam, and (f) relating the amplitude and the change in phase angle to a property of the surface of the sample. A feedback system is utilized which regulates the total force imposed by the fine tip onto the surface of the sample so that the amplitude of the detector response is maintained constant. Because the force does not depend on the topography of the sample, the average cantilever deflection is directly related to the mechanical property of the surface of the sample and is not affected by any topographical feature present on the surface of the sample.

2 Claims, 1 Drawing Sheet

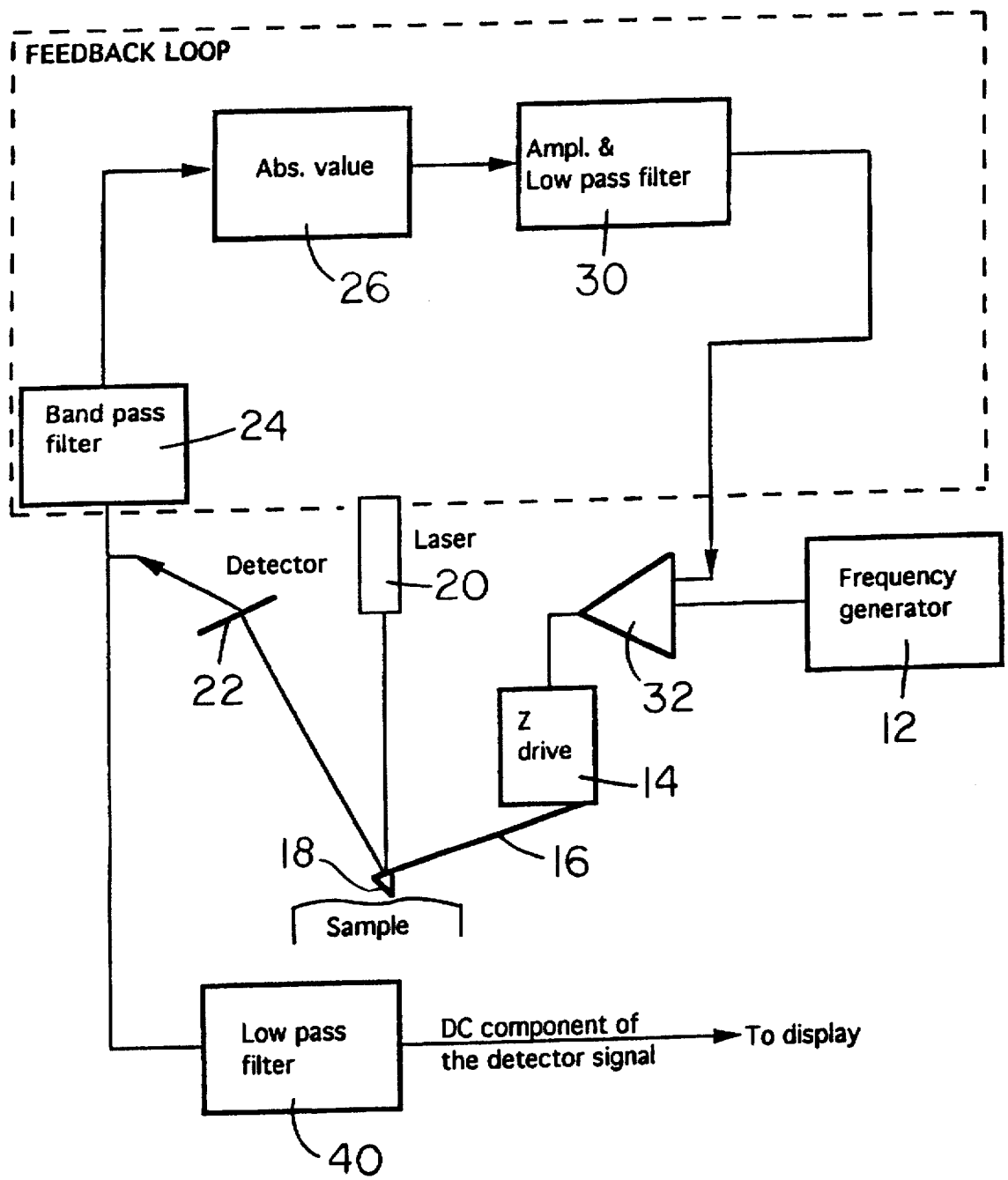

METHOD FOR MAPPING MECHANICAL PROPERTY OF A MATERIAL USING A SCANNING FORCE MICROSCOPE

BACKGROUND OF THE INVENTION

1. Field of the Invention

The present invention relates generally to methods for determining mechanical properties of the surface of a material by microscopic scanning, and more particularly relates to determination of viscoelastic properties of the surface of a material using a scanning force microscope.

2. State of the Art

Scanning force microscopy (also called atomic force microscopy) has become a useful technique to image the topography of the surface of a sample in a variety of media without the need for extensive sample preparation. Recently the scanning force microscope has been used to image the topography of materials, with the ability to resolve topographic features to 10 nm width. These studies have been performed most successfully on relatively flat Langmuir-Blodgett films or self-assembled monolayers. Less success has been reported in distinguishing the microphase separated structure of polymer films with more apparent topographical features.

Intrinsic problems of contact scanning force microscopy lie in the deformation of the sample under the load exerted by the tip of the scanning force microscope and in the frictional property of the tip-sample contact. The topography of a sample as observed by a scanning force microscope is affected by such deformation and friction and, thus, often yields false information about the properties of the surface of the sample. These same factors adversely influence determinations of mechanical properties of the sample made with the aid of a scanning force microscope.

The scanning force microscope has been used to measure mechanical properties of surfaces, but such studies have generally been limited to samples possessing little or no topography, i.e., on flat surfaces. Studies on samples having more topographical features have produced spatial maps of compliance that were largely affected adversely by the topography of the sample.

Mapping the local compliance of a surface has been typically performed by a force modulation method. In such a scanning method, a small sinusoidal modulation is superimposed to the current z-position of the piezoelectric element controlling the tip-sample separation distance. With the tip in contact with the sample, this z-modulation imposes a small variation of tip loading force exerted onto the sample. In a standard version of this method, the feedback regulation loop maintains a constant average position of the cantilever, i.e., constant average load or isoforce, during the scanning process by adjusting the position of the sample relative to the cantilever. Depending on the average loading force and the compliance of the tip-sample area, the tip of the scanning force microscope indents the sample in a sinusoidally varying fashion. The dept of indentation is smaller for stiff sample areas that it is for the compliant areas. The detection of the indentation depth changes are made using optical lever techniques in conjunction with the scanning force microscope. The variation of the indentation depth (or the modulated cantilever angle change) are used to create the map of the sample local compliance. This method has been used quite successfully to map local compliance of the surface of a flat surface, but the method has not been found useful in mapping surfaces that are more topographically featured. It would be highly advantageous to provide an improved method of using a scanning force microscope to which is capable of accurately mapping mechanical properties of a sample, such as local compliance, when the surface of the sample has topographical features, i.e., is not flat.

OBJECTIVE AND BRIEF DESCRIPTION OF THE INVENTION

The principal objective of the present invention is to provide a novel improvement in the force modulation method of imaging a surface of a material using a scanning force microscope wherein mechanical properties of the sample can accurately be determined even on samples having surfaces that are topographically featured, i.e., not flat. The improvement comprises using a feedback system that regulates the total force imposed by the tip of the scanning probe microscope onto the surface of the sample so that the amplitude of the detector response, rather than the cantilever deflection, is maintained constant. Since the force does not depend in any way on the sample topography, the average cantilever deflection is then directly related to the sample surface property being measured and is not affected by any topographic feature present on the surface of the sample.

The present invention provides an improvement in a method for mapping a mechanical property of a surface of a sample with a scanning force microscope. The basic method comprises the steps of (a) scanning a fine tip in contact with the surface of the sample within a predetermined scan area, the fine tip being supported on an end of a cantilever beam, (b) applying a loading force on the surface of the sample by the fine tip, (c) using a constant frequency sine wave to oscillate the cantilever beam relative to the surface of the sample, (d) measuring a detector response of the fine tip at the end of the cantilever beam, (e) determining an amplitude of the detector response and a change in phase angle of the detector response relative to the sine wave used to oscillate the cantilever beam, and (f) relating the amplitude and the change in phase angle to a property of the surface of the sample.

The improvement in the basic method, as provided by the present invention, comprises utilizing a novel feedback system in which an AC component of the detector response is determined and the absolute value of the AC component is detected. The absolute value of the AC component is then compared with a preset, absolute amplitude of the sine wave that is used to oscillate the cantilever beam. A feedback signal is generated that corresponds to the comparison of the absolute value of the AC component with the preset, absolute amplitude of the sine wave.

The feedback signal is used to control the applied loading force imposed on the surface of the sample by the tip so that the amplitude of the detector response is maintained substantially constant as the tip scans the surface of the sample. A DC component of the detector response is determined, and the DC component is used to relate the applied loading force imposed on the surface of the sample to the mechanical property of the surface of the sample immediately below the tip.

The improved method of the present invention uses a constant frequency sine wave signal to oscillate the cantilever beam having an end-mounted sharp probe or fine tip in contact with the surface of the material being tested. A detector is provided to monitor the movement of the fine tip at the end of the cantilever. The surface property of the material affects the amplitude of the detector response and changes its phase angle relative to the sine wave signal that is used to drive the cantilever beam. Accordingly, the amplitude and the phase of the detector response can be used to map a particular surface mechanical property of the sample while the probe is rastered across the surface in an x–y fashion.

Additional objects and features of the invention will become apparent from the following detailed description, taken together with the accompanying drawings.

In a preferred embodiment of the present invention, the sine wave signal is used to oscillate the cantilever beam in a direction substantially normal to the surface of the material being tested so as to indent the sharp tip on the end of the cantilever beam into the sample. Hence the obtained information is related to the surface viscoelastic property of the material. In principle, the same approach can be used to drive the cantilever beam in any other direction such that the related amplitude and phase angle change will be affected by a particular surface property other than viscoelasticity, such as dynamic friction, shear modulus or other property.

As mentioned previously, the feedback system of the present invention regulates the total force imposed by the probe onto the sample surface so that the amplitude of the detector response, rather than the cantilever deflection, is maintained substantially constant. Since the force does not depend in any way on the sample topography, the average cantilever deflection is directly related to the surface property of the sample that is being evaluated, such as the surface viscoelasticity, and is not effected by any topographical feature present on the surface.

THE DRAWINGS

A preferred embodiment of the present invention representing the best mode presently contemplated of carrying out the invention is illustrated in the accompanying drawings in which the single figure is a block diagram of the improved method of using a scanning force microscope utilizing the novel feedback system of the present invention.

DETAILED DESCRIPTION OF THE ILLUSTRATED EMBODIMENT

The surface properties of any material may not be uniform on a very small scale because of its potentially heterogeneous composition, surface contamination, phase-separation and other unknown effects. The contact scanning force microscope has been very useful in evaluating surface topography of samples having hard surfaces. However, many samples, like majority of polymers, thin organic films and biological ad-layers are simply too soft for the contact scanning force microscope, and any topography present on the surfaces of these materials washes off due to the overwhelming forces occurring between the scanning probe tip and the surface of the sample.

Hence, the true surface properties of soft samples are elusive and experimentally inaccessible. The use of the non-contact scanning force microscope has been proposed to circumvent this problem, albeit at the expense of spatial resolution. A technique, which is not affected by the surface topography, is needed for evaluating the property of soft surfaces. In accordance with the present invention, there is disclosed an improved method of using a contact scanning force microscope which eliminates the effects of topography of any sample from the signal that can be directly related to the surface mechanical property that is being studied, such as local compliance, surface viscoelasticity and potentially many others.

The improved method is based on using a constant frequency sine wave signal that oscillates the cantilever beam having an end-mounted, sharp probe or tip in contact with the surface of the material being tested. The surface property of the material affects the amplitude of the response from the detector that monitors and detects the movement of the probe or tip at the end of the cantilever beam. In addition, the phase angle of the detector response relative to the driving sine wave signal is changed. The amplitude of the detector response and the phase change can be used to map a particular mechanical property of the surface of the sample while the probe or tip rasters over the surface of the sample in an x–y fashion.

The method of the present invention is shown schematically in the single figure of the drawing. A frequency generator 12 oscillates the z-piezo drive 14 at a specific, preset frequency. The z-piezo drive 14 holds the cantilever beam 16 and oscillates the cantilever beam 16 at the same specific, preset frequency. Mounted at the end of the cantilever beam 16 is a sharp probe or tip 18. The tip 18 is in contact with the surface of the sample.

As the oscillation is transmitted onto the sample from the tip 18, a laser beam from laser 20 is focussed on the cantilever end and in its reflected part contains the information about the amplitude of the oscillatory displacement of the tip 18 that is indenting the surface of the sample. A position sensitive detector 22 receives the reflected laser beam, and a signal from the detector 22 is sent to two separate electronic circuits.

The signal that is sent to the feedback circuit first passes through a band pass filter 24 to define an AC component of the detector response. The AC component is then processed through an absolute value circuit 26 and an amplifier and low pass filter 30 to generate a feedback control signal representative of the absolute value of the AC component of the detector response. The feedback control signal is then compared by comparator 32 with a preset value which amounts to a fraction of the absolute amplitude of the sine wave that is generated by the frequency generator 12.

The preset value which the comparator 32 uses to compare to the feedback control signal must be at least slightly smaller than the absolute amplitude of the sine wave that is generated by the frequency generator 12, and it also must be at least slightly greater than zero. As a matter of practice, the preset value which the comparator 32 uses to compare to the feedback control signal can be anywhere from one or two percent up to ninety-nine percent of the absolute amplitude of the sine wave that is generated by the frequency generator 12. The comparator 32 produces a feedback signal that corresponds to the comparison of the absolute value of the AC component of the detector response with the preset value mentioned above.

The feedback signal is used to control the applied loading force imposed on the surface of the sample by the tip 18. This is accomplished by having the feedback signal control the position of the z-piezo drive relative to the surface of the sample being tested. The feedback system controls the applied loading force imposed on the surface of the sample so that the amplitude of the detector response is maintained substantially constant as the tip 18 scans the surface of the sample. The DC component of the detector response is directed to display circuitry that is not shown in the drawing. The DC signal is used to relate the applied loading force imposed on the surface of the sample to the mechanical property of the surface of the sample at a point immediately below the tip 18.

In accordance with the present invention, the amplitude of the detector response, i.e., the amplitude of the oscillatory displacement of the tip 18, is maintained constant by the feedback system described above which changes the z-position of the cantilever beam 16 with respect to the surface of the sample. This variation of the z-position changes the force that the tip 18 exerts on the surface of the sample. The average force is determined by the average deflection of the cantilever beam 16, i.e., by its angle change relative to its resting position when the cantilever beam 16 and the tip 18 are far away from the sample.

The DC component of the detector response contains the information about the average cantilever deflection. The DC component can be determined or obtained by passing the signal from the position detector 22 through a low pass filter 40. The DC component contains only the information about a given surface property, such as its viscoelasticity.

The feedback system of the present invention regulates the total force imposed by the tip 18 onto the surface of the sample in such a way that the amplitude of the detector response, rather than the cantilever deflection, is maintained constant. Hence, the feedback system eliminates the dependency of the total force on the sample topography and the average cantilever deflection is directly related to the sample surface viscoelasticity. By collecting the average deflection value for every x–y position of the surface of the sample during the rastering process, the improved method of the present invention provides a map of sample surface viscoelasticity free of any effects of topography. The measurements can be performed in any transparent medium which is another advantage over non-contact scanning force microscope methods which are generally limited to ambient air conditions.

Although a preferred embodiment of the improved method of the present invention has been illustrated and described, it is to be understood that the present disclosure is made by way of example and that various other embodiments are possible without departing from the subject matter coming within the scope of the following claims, which subject matter is regarded as the invention.

What is claimed is:

1. In a method for mapping a mechanical property of a surface of a sample with a scanning force microscope, wherein said method comprises the steps of (a) scanning a fine tip in contact with the surface of said sample within a predetermined scan area, said fine tip being supported on an end of a cantilever beam, (b) applying a loading force on the surface of said sample by said fine tip, (c) using a constant frequency sine wave to oscillate the cantilever beam relative to said surface of said sample, (d) measuring a detector response of the fine tip at the end of the cantilever beam, (e) determining an amplitude of the detector response and a change in phase angle of the detector response relative to the sine wave used to oscillate the cantilever beam, and (f) relating said amplitude and said change in phase angle to a property of said surface of said sample, the improvement comprising determining an AC component of said detector response;

determining the absolute value of said AC component;

comparing said absolute value of said AC component with a preset value which is greater than zero and at least slightly less than the absolute amplitude of said sine wave that is used to oscillate the cantilever beam;

generating a feedback signal that corresponds to the comparison of said absolute value of the AC component with said preset value;

using the feedback signal to control the applied loading force imposed on the surface of said sample by said tip so that the amplitude of the detector response is maintained substantially constant as the tip scans the surface of said sample;

determining a DC component of said detector response; and using the DC component to relate said applied loading force imposed on the surface of said sample to the mechanical property of the surface of said sample immediately below said tip.

2. A method in accordance with claim 1 wherein the cantilever beam is oscillated in a direction substantially normal to the surface of the sample, and the mechanical property of the surface of the sample that is mapped is the surface viscoelastic property.

* * * * *